United States Patent [19]
Ardry et al.

[11] 3,936,434
[45] Feb. 3, 1976

[54] CYTOBIOTIC GLOBULINS FOR KIDNEY TREATMENT

[75] Inventors: Robert Ardry, Clamart; Michel Robilliart, Paris, both of France

[73] Assignee: Omnium Financier Aquitaine pour l'Hygiene et la Sante (Sanofi), Courbevoie, France

[22] Filed: Apr. 23, 1973

[21] Appl. No.: 353,890

Related U.S. Application Data

[63] Continuation-in-part of Ser. No. 312,021, Dec. 4, 1972, which is a continuation-in-part of Ser. No. 111,760, Feb. 1, 1971, abandoned, which is a continuation of Ser. No. 766,313, Oct. 9, 1968, abandoned.

[30] Foreign Application Priority Data

Oct. 10, 1967 France ........................... 67.123862

[52] U.S. Cl. ............ 260/112 B; 260/112 R; 424/85; 424/88; 424/103; 424/177
[51] Int. Cl.² ..................... A61K 37/06; C07G 7/00
[58] Field of Search ..................... 260/112 B, 112 R

[56] References Cited
FOREIGN PATENTS OR APPLICATIONS
1,547,619  11/1968  France

OTHER PUBLICATIONS
Chem. Abstracts, Vol. 73, 1970, 64435k, Ardry et al.

Primary Examiner—Howard E. Schain
Attorney, Agent, or Firm—Karl F. Ross; Herbert Dubno

[57] ABSTRACT

A cytobiotic of cytogenic globulin for the treatment of kidney disorders in mammalian subjects and for prophylaxis against kidney-cell degeneration and as a cell regenerative treatment, comprises the product obtained by recovering renal tissue from slaughterhouse animals, obtaining an extract therefrom and using this extract to innoculate a horse and obtain an immunological response plasma. From the latter zinc salt or ammonium sulfate is used to obtain a precipitate which, after dialysis, leads to a dialysate which contains the effective globulins.

2 Claims, 4 Drawing Figures

CYTOBIOTIC GLOBULINS FOR KIDNEY TREATMENT

CROSS REFERENCE TO RELATED APPLICATIONS

This application is a continuation in part of copending application Ser. No. 312,021 filed Dec. 4, 1972 which is a continuation in part of copending application Ser. No. 111,760 filed Feb. 1, 1971 (now abandoned) which is a continuation of application Ser. No. 766,313 filed Oct. 9, 1968 (now abandoned).

FIELD OF THE INVENTION

Our present invention relates to a cytobiotic globulin extract, pharmacological compositions containing these globulins, a method of treatment using the globulin and a method of making these compositions.

BACKGROUND OF THE INVENTION

While it has long been known that extracts from living organisms, and especially animal organs, contain recoverable substances with therapeutic properties for the treatment of animals and humans, prior-art systems for recovering substances with therapeutic properties have heretofore concentrated, mostly on the extraction of hormones and hormone-like products for this purpose.

We have found that it is possible to recover cytobiotic or cytogenic products from animal kidneys which have a surprising effect upon corresponding human or other animal kidneys with respect to regeneration and revivication of the tissues and cells thereof. The compounds or compositions with which the present invention is concerned are globulins or proteinaceous materials which manifest cytogenic or cell-regeneration characteristics upon recovery from animal kidneys in the manner set forth hereinbelow and when used as described.

Our invention is of special importance in connection with tissue regeneration or protection to replace removed or dead kidney tissue upon rectal or parenteral administration.

More especially, the products of the present invention have utility, in parenteral injection in man and in animal, for protecting the renal tissue against alterations caused by administration of different nephrotoxic substances.

OBJECTS OF THE INVENTION

It is the principal object of the present invention to provide an improved method of extracting cytobiotic and cytogenic globulins, having renal cell-regenerating characteristics when used in the treatment of living organisms, from the kidneys of animals.

Another object of our invention is the provision of a method of obtaining a cytobiotic globulin for the treatment of lesions, and the like of renal tissue for promoting cell growth or regeneration.

Yet another object of this invention is the provision of a method of treating living organisms to promote kidney cell protection and regeneration.

Still a further object of our invention is to provide improved compositions for such treatment.

DESCRIPTION OF THE INVENTION

We have now found that it is possible, through a series of relatively simple steps, to obtain from animal organs taken at the slaughterhouse, proteinaceous materials or globulins which, in the extracted or recovered form, manifest a high degree of specific cytobiotic or cytogenic activity when used in the treatment of the corresponding organs of living patients.

Our invention yields in the final analysis cytobiotic globulins in the form of a greyish-white powder which can be used in sera or in various excipients for the direct treatment of the animal subject, to derive compounds which have the highly specific cytobiotic property mentioned earlier. When the terms "cytobiotic" and "cytogenic" are used herein, it should be understood that it is intended to include several forms of cell activity, including the protection of cells and the regeneration of tissues constituted by the cells whose growth is promoted. The expressions also are intended to connote either the revivication of tissue or the improvement of tissue tone by cell-growth stimulation.

More specifically, we have now found that it is possible to recover from healthy-animal kidneys as obtained from slaughter-houses or like sources, a soluble antigenic extract, to immunize an animal of another species by repeated injections of this extract, to collect the blood of the hyperimmunized animal and to recover from the blood thus collected, all the protein fractions carrying immunological properties or total immuneglobulins, and finally to select from the total immuneglobulins the most stable globulins which present the optimum cytobiotic activity.

The globulins have no antagonistic characteristics and are nontoxic in the treatment of humans or other animals and do not induce, in turn, rejection phenomena; but they manifest specific tropism for tissues corresponding to the homologous tissues from which they originally derive, or rather exert a regenerative action upon such tissues so as to restore or promote restoration of deteriorated or dead tissue to thereby allow early restoration of the normal function of the organ.

GENERAL DESCRIPTION OF THE METHOD

A. Preparation of an antigenic extract from animal kidneys

The method of recovery of the globulins of our present invention comprises initially the subdivision of the healthy-animal kidneys and preferably the embryo kidneys, by chopping, mincing or grinding, followed by washing of the subdivided mass with a saline solution (preferably 0.9% aqueous sodium chloride by weight) to eliminate residual blood while the organ preferably is used directly after it is removed from the animal carcass at the slaughterhouse. We have also found it to be feasible to temporarily store the organ by freezing it immediately after it has been taken from the carcass. In either case, the subdivision and blood-removal steps proceed as described.

After eliminating any residual blood, the subdivided organ is pulverized in a mixer, blender or other similar apparatus and is then suspended in ten times its weight of a 0.9% by weight aqueous saline solution at ambiant (room) temperature. The suspension is agitated for a period of one hour, whereupon the suspension is centrifugated, the soluble portion is kept aside and the insoluble portion is withdrawn and subjected to freezing below − 20° C to effect cell rupture. After thawing, the insoluble fraction is again suspended in about ten times its weight of 0.9% by weight aqueous sodium chloride solution, agitated with the insoluble part being recovered, and washed until the washing liquid no longer contains any soluble materials.

The soluble portion prepared as described herein above is the antigenic extract, and the insoluble residue of homogenized tissue is used in a subsequent stage of the process.

B. Preparation of the total Immune Globulins

The technique for obtaining solutions of cytobiotic globulins can be considered in two basic steps, namely isolation of the total immune globulins and selection of the most effective globulins from the collection of immune globulins produced in the first stage.

After it has been prepared as described earlier an antigenetic extract is then injected into the host animal (horse), and the blood of this immunized animal is thereafter collected in accordance with usual serum-recovery techniques, on an anticoagulant, of which the final concentration is about 0.02M. The plasma is then separated and treated by an ammonium sulphate procedure or a metallic salt procedure, as discussed below, in order to remove impurities.

In the ammonium sulphate technique, the plasma is combined with an aqueous solution of saturated ammonium sulphate (1.025 in the ammonium salt) to yield a precipitate which is removed by centrifugation and decanted. The ammonium sulphate concentration is then raised to 1.56 M by the addition of a saturated solution of the salt, and this precipitate collected and washed with 1.56 M aqueous ammonium sulphate. The washed precipitate is dispersed in distilled water and subjected to dialysis against distilled water to complete disappearance of ammonium salt and yields a globulin capable of undergoing selection in the second stage.

In the metal-salt technique, the plasma is diluted with three volumes of aqueous sodium chloride with a concentration of about 0.9% by weight, although the precise concentration used will depend upon the animal species from which the blood is derived. A zinc salt is then added to a concentration of 10 millimoles. The resulting precipitate is separated by centrifugation and filtration. The zinc salt is then added to the filtrate to raise the concentration to 18.6 millimoles and a basic aminoacid is added to a concentration of 0.43 millimoles. After the centrifugation, the new precipitate is recovered, washed with distilled water (one volume for every three volumes of the plasma initially used) and the paste dialyzed in fresh distilled water for 24 hours against distilled water. Then the product may undergo the selection stage mentioned earlier.

C. Cytobiotic Globulin Selection

Selection may be done on a two-part basis, in the first, the total immune protein is treated in a solution by adding sodium chloride and sodium hydroxide to the suspension resulting from dialysis against distilled water so that the proteinic concentration is finally about 5% by weight, the pH is about 7.3 ± 0.3 and the ionic strength is about 0.6.

To the mixture which some of the proteins are insoluble, Muchar C190 filtering-aid active-carbon powder is added in an amount of 1 to 2% by weight, the mixture being permitted to stand. After a period of one hour, the liquid is decanted, subjected to centrifugation with the supernatant liquid being filtered on a clarifying filter.

The solution is put into contact with the insoluble residue of homogenized tissue ("homogenate") from the organ used for the formation of the antigenic product used to inoculate the horse. The homogenate, which is specific to the antibodies contained in the globulin, is previously subjected to treatment with a citrate solution having a straight concentration of 0.15 M and a pH of 3.1 ± 0.1, the homogenate is thereafter washed with the solution of 0.15 M sodium chloride buffered to pH 7.5 ± 0.3.

After standing in contact with the homogenate, the immune globulin solution is decanted and the insoluble tissue homogenate containing adsorbed globulins is eluted with a citrate solution (0.15 M to pH 3.1); then the eluate is neutralized to pH 7.5 ± 0.3. The insoluble part is removed and the solution subjected to dialysis against the sodium chloride solution of 0.15 M. When the protein concentration is low, we may lyophilize the dialyzed solution and then dissolve the lyophilized protein in sodium chloride solution (0.15 M) with a pH adjusted to 7.5. The globulin solutions are subjected to filtration through sterilized patches (in a sterile atmosphere) and then lyophilized.

EXAMPLE 1

Six liters of immunized horse blood are collected with 100 ml of a 33% aqueous solution of trisodium citrate as an anticoagulant and blood plasma is separated by methods known per se. The horse blood is obtained from a horse injected with a soluble antigenic extract obtained from the slaughterhouse kidneys as described hereinabove.

A saturated solution of ammonium sulfate in water is made up and added in an amount of one volume of each three volumes of the plasma and the resulting precipitate is removed by centrifugation and decanting of the supernatant liquid. To this liquid we add 220 ml of a saturated solution of ammonium sulfate per liter, thereby forming a second precipitate which is washed with 38 parts by weight of a citrate solution of ammonium sulfate and 62 parts by weight of distilled water.

The washed precipitate is dispersed in distilled water and dialysed against distilled water to complete disappearance of ammonium sulfate. The resulting suspension is adjusted at a protein concentration of 5%, a pH of 7.5 ± 0.3 and an ionic strength of 0.06 by addition of 3.5 g of sodium chloride for each liter of the suspension, and the exact quantity of a solution of sodium hydroxide N. This treatment eliminates inactive proteins and produces a globulin solution which is treated with 1 to 3% by weight of active carbon (NUCHAR C190) and permitted to stand for about an hour, followed by centrifugation, decantation and filtering of the supernatant liquid in a clarifying filter.

A homogenate of the kidneys prepared at the same time as the antigenic extract is purified as described in general terms earlier. The macerated homogenate is treated before use with a sodium citrate solution at a concentration of 0.15 M and a pH of 3.1 ± 0.1, followed by washing with a sodium chloride solution buffered to pH 7.5. ± 0.3 and with a concentration of 0.15 M. This washed homogenate and globulin solution obtained after carbon filtration, are permitted to stand together. After elimination of the solution which contains non specific globulins, the homogenate, upon which the specific, cytobiotic globulins have been absorbed, is subjected to elution with a sodium citrate solution of 0.15 M at pH 3.1, the eluate being then adjusted to a pH of 7.5. ± 0.3. The insoluble portion is removed from the solution which is dialysed against a sodium chloride solution at 0.15 M.

This solution is filtered on a sterilized milliporous filter in a sterile atmosphere and can be lyophilized to yield the globulin powder having the properties mentioned earlier.

EXAMPLE 2

One volume of horse plasma, obtained as in Example 1 is combined with three volumes of 0.9% sodium chloride solution to which 30 ml of 9.6% zinc sulphate solution in diluted water is added per liter of the horse plasma sodium chloride mixture.

After discarding of the precipitate each liter of the filtrate is combined with 21 ml of an aqueous solution of zinc sulfate at 9.6% concentration and 5 ml of a 6.5% aqueous solution of glycine. Dialysis is carried out as in Example 1 with final recovery of the globulins as theredescribed.

PHARMACOLOGICAL PROPERTIES AND EFFICACITY

The cytobiotic globulin powder prepared as described in Example 1 was greyish-white, light-weight, highly soluble in water and soluble in physiological serum. Tests of the cytobiotic globulins were carried out to determine its action, upon regeneration or protection of the renal tissue and the toxicity and efficacy of the product in the treatment of animals and humans.

In toxicity tests, the globulins have shown no acute toxicity in mice and guinea pigs, no chronic toxicity in rabbits and guineaa pits, no antibody reaction when tested in gelose against various human, amniotic and porcine cells, no antibody reaction against a macerated mixture of amniotic human cells and pig-kidney cells and no teratogenic activity in the mouse, rat or rabbit.

The globulins prepared according to the present invention have a protective action against the renal alterations induced by different nephrotoxic substances, as shown by the following pharmacological tests.

A. PROTECTION AGAINST LESIONS INDUCED BY STREPTOMYCIN AND DIHYDROSTREPTOMYCIN IN THE RAT

Two similar batches of rats received, by parenteral route,
the first (control No. 1) a dose of 40 mg/kg of body weight of streptomycin,
the second, (control No. 2) a dose of 40 mg/kg of body weight of dihydrostreptomycin, before, then after having undergone a partial binephrectomy.

Two other batches of rats received the same doses of streptomycin and dihydrostreptomycin respectively as the two previous batches, but received at the same time, by parenteral route, a dose of 0.5 mg of lyophilized globulins dissolved in physiological serum, 3 times per week.

The rats were sacrificed after 8 weeks, and histological sections were made in the remaining renal stump, and coloured with tetrachrome (alizarine blue) and with P.A.S. "alcyon" blue orange.

These histological sections are shown in the accompanying FIGS:

FIG. 1 shows a section of kidney of the control group No. 1 (having received streptomycin), FIG. 2 shows a section of kidney of an animal having received streptomycin and globulins according to the invention, FIG. 3 shows a section of kidney of an animal having received digydrostreptomycin and globulins according to the invention, FIG. 4 shows a section of kidney of an animal, control No. 2 (having received dihydrostreptomycin).

FIG. 1 shows a discreet attack of the Malpigli glomerules and proliferating tubular lesions.

FIG. 4 shows proliferating glomerular lesions with progressive disappearance of the urinary space, and a tubular attack with disappearance of the ciliated edge of the proximal tubes.

Figure 2:
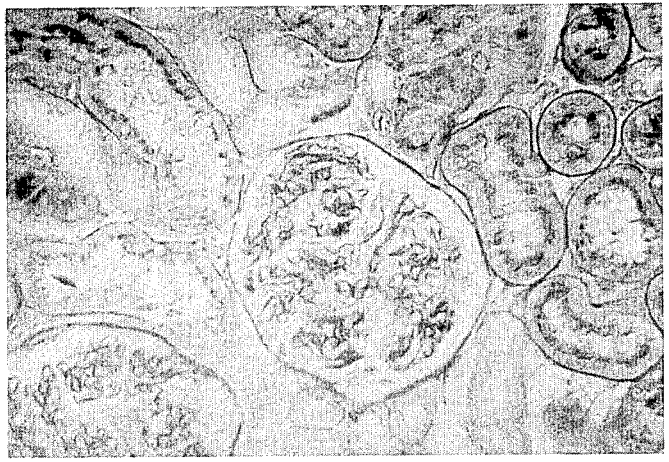
Figure 1:
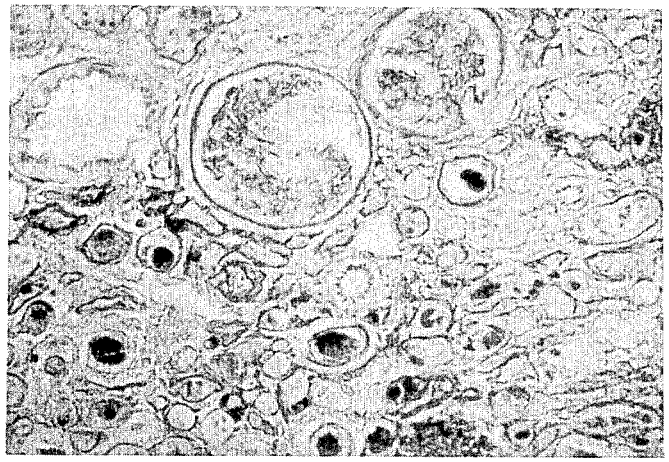
FIGS. 1 and 4 show the renal alterations produced in the controls for the nephrotoxic substances (streptomycin and dihydrostreptomycin).
Figure 3:
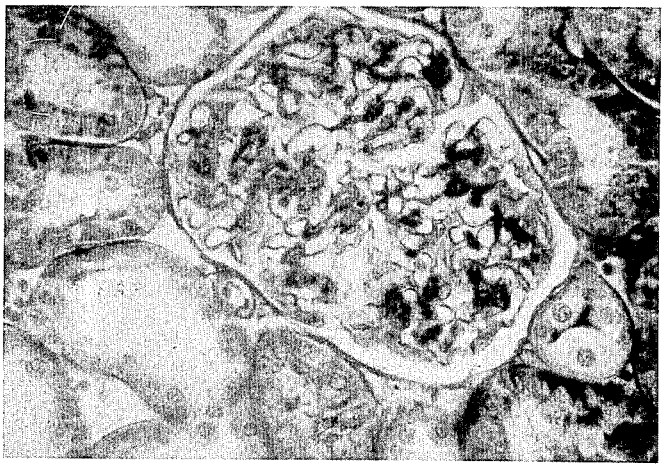
Figure 4:
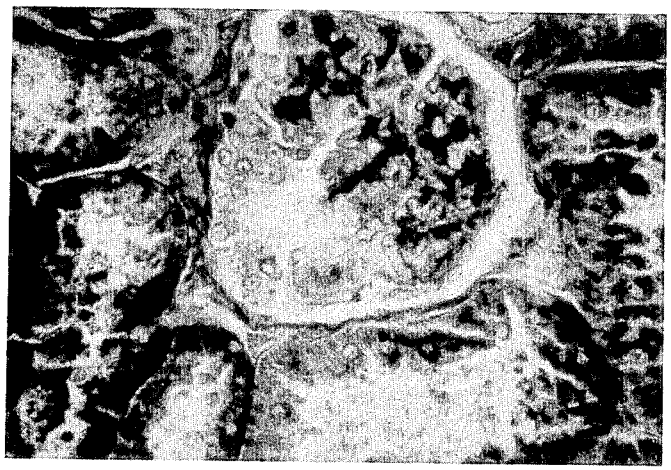

On the other hand, FIGS. 2 and 3 show that the glomerular and tubular appearance is normal in the subjects treated with the globulins according to the invention, this showing that the product according to the invention has protected the kidney against the renal alterations produced by streptomycin and dihydrostreptomycin.

B. PROTECTION AGAINST THE LESIONS OF EXPERIMENTAL AMYLOSE INDUCED BY SODIUM CASEINATE IN THE RABBIT

Rabbits distributed in two batches are intoxicated with sodium caseinate by sub-cutaneous injections for three months in order to provoke an experimental amylose.

In one of the batches, the animals receive the caseinate alone at a dose of 3.5 ml of an 8 % solution in distilled water, by sub-cutaneous route; this is the control batch.

In the other, the rabbits receive, in addition, twice a week, the globulins according to the invention at a dose of 0.5 mg/kg, by intravenous route.

After the period, about 13 weeks, the animals are sacrificed and the organs examined are the liver, spleen, kidney.

In all the controls, these three organs are overrun with amylose visible on the sections in immunofluorescense (coloring with Tioflavine T). There is no glomerule undamaged by amylose in the kidney; the liver and spleen are totally affected.

In the treated animals, the amylose remains identical in the liver and spleen, thus revealing the degree of intoxication of the animals; however, in the kidneys, there is no trace of amylose; the specific globulin of the kidney has protected this organ, and this organ alone, this showing both the efficiency and specificity, with respect to the kidney, of the product according to the invention.

CLINICAL TESTS

The product according to the present Application has been tested clinically in the treatment of recent glomerulopathies and chronic nephropathies.

The following was administered:
1. 20 mg in solution in physiological serum, in I.M. injections, every two days for 30 days.
2. or 25 mg, in the form of suppositories, every day for thirty days.

After one month of treatment, the experimenters comparing the results usually obtained in the treatment of chronic nephropathies and those obtained with the globulin, conclude:
1. a considerable improvement in the renal functioning as well as slowing down of the development of chronic nephropathies which would otherwise lead to an irreversible renal insufficiency.

2. the cure of recent glomerulopathies.

We claim:

1. A method of producing cytobiotic globulins comprising the steps of:
   1. macerating a ground-kidney organ of a healthy slaughter-house animal or preferably of an embryo in an aqueous solution containing about 0.9% by weight sodium chloride, and thereafter centrifugating the suspension to obtain a soluble antigenic extract and an insoluble tissue homogenate;
   2. inoculating a horse with said antigenic extract to induce an immunological response in the blood of the inoculated horse;
   3. withdrawing blood from said inoculated horse and separating plasama therefrom;
   4. extracting a globulin-containing liquid from said plasma by combining said plasma with an aqueous saturated solution of ammonium sulfate to produce a precipitate; separating a solution from the last-mentioned precipitate and treating it with a further quantity of ammonium sulphate to form a further precipitate; forming a paste of said further precipitate in distilled water and dialyzing said paste to complete disappearance of ammonium salts; and recovering a further dialysate constituting said globulin-containing liquid extract;
   5. adding water, sodium chloride and sodium hydroxide to said globulin-containing liquid to adjust it to a pH of about 7.3, an ionic strength of 0.16 and a protein concentration of 5%;
   6. contacting adjusted globulin-containing liquid with tissue homogenate which has been previously treated with a sodium citrate solution 0.15 M having a ph of about 3.1 and washed with a sodium chloride solution 0.15 M having a pH of about 7.5;
   7. decanting the liquid and eluting globulins adsorbed onto tissue homogenate with a sodium citrate solution 0.15 M having a pH of 3.1;
   8. adjusting the elution solution to a pH of 7.5, separating the precipitate and dialyzing the elution solution against a sodium chloride solution 0.15 M;
   9. lyophilizing the dialyzed solution to obtain cytobiotic globulins.

2. A method of producing a cytobiotic globulins comprising the steps of:

macerating a ground kidney organ of a healthy slaughter-house animal in an aqueous solution containing about 0.9% by weight sodium chloride, and thereafter treating and centrifugating the suspension to obtain a soluble antigenic extract and an insoluble tissue homogenate;

inoculating a horse with said antigenic extract to induce an immunological response in the blood of the inoculated horse;

withdrawing blood from said inoculated horse and separating plasma thereof;

extracting a globulin-containing liquid from said plasma by diluting said plasma with an aqueous sodium chloride solution and thereafter treating same with a zinc salt to form a precipitate; recovering the liquid from the last-mentioned precipitate and treating it with a further quantity of said zinc salt and a basic amino acid to form a further precipitate; dizlyzing said further precipitate to form said globulin-containing liquid;

adding water, sodium chloride and sodium hydroxide to said globulin-containing liquid to adjust it to a pH of about 7.3, an ionic strength of 0.05 and a protein concentration of 5%;

contacting adjusted globulin-containing liquid with tissue homogenate which has been previously treated with a sodium citrate solution 0.15 M having a pH of about 3.1 and washed with a sodium chloride solution 0.15 M having a pH of about 7.5.
;

decanting the liquid and eluting globulin absorbed onto tissue homogenate with a sodium citrate solution 0.15 M having a pH of 3.1;

adjusting the elution solution to a pH of 7.5, separating the precipitate and dialyzing the elution solution against a sodium chloride solution 0.15 M;

lyophilizing the dialyzed solution to obtain cytobiotic globulins.

* * * * *